United States Patent [19]

Halm et al.

[11] Patent Number: 4,946,978

[45] Date of Patent: * Aug. 7, 1990

[54] METHOD OF DIRECT PROCESS PERFORMANCE IMPROVEMENT VIA CONTROL OF SILICON MANUFACTURE

[75] Inventors: Roland L. Halm, Madison, Ind.; Oliver K. Wilding, Jr., Louisville, Ky.

[73] Assignee: Dow Corning Corporation, Midland, Mich.

[*] Notice: The portion of the term of this patent subsequent to Nov. 7, 2005 has been disclaimed.

[21] Appl. No.: 944,317

[22] Filed: Dec. 22, 1986

[51] Int. Cl.$^5$ ................................................ C07F 7/16
[52] U.S. Cl. .................................................... 556/472
[58] Field of Search ........................................ 556/472

[56] References Cited

U.S. PATENT DOCUMENTS 4,520,130  5/1985  Hashiguchi et al. .
4,602,101  7/1986  Halm et al. .......................... 556/472

OTHER PUBLICATIONS

Dosaj, V. D., et al., "High Purity Silicon for Solar Cell Applications", 1208 J. of Metals, vol. 30, No. 6, (1978/06).

Primary Examiner—Paul F. Shaver
Attorney, Agent, or Firm—Robert L. McKellar; James E. Bittell

[57] ABSTRACT

This invention discloses a method of treating silicon with non-volatile, phosphorous compounds to allow the silicon to be used in the direct process for the manufacture of alkylhalosilanes. The treatment of the silicon is carried out by feeding phosphorous compounds to the silicon during or after refining.

18 Claims, No Drawings

METHOD OF DIRECT PROCESS PERFORMANCE IMPROVEMENT VIA CONTROL OF SILICON MANUFACTURE

SUMMARY OF THE INVENTION

This invention deals with the use of certain nonvolatile, phosphorous compounds in the production of silicon used in the direct process to produce alkylhalosilanes. The phosphorous, in the reduced state, acts as a promoter in the direct process when used in certain quantities. Silicon containing the phosphorous can be used in the direct process when the level of reduced phosphorous compounds is controlled in the silicon as it is being refined.

BACKGROUND OF THE INVENTION

This invention deals with a method of improving the performance of a process for the manufacture of alkylhalosilanes. This invention deals mainly with the treatment of silicon, which is used in the direct process for the production of alkylhalosilanes. More particularly, this invention deals with a method of controlling the level of phosphorous promoters in silicon used in the direct process, in order that the direct process in which the treated silicon is used is enhanced in terms of reactivity and selectivity of direct process reactions.

The benefits to be derived by the use of this invention are increased alkylhalosilane yields, selectivity of certain alkylhalosilanes over other, less preferred alkylhalosilanes and, overall high utilization of raw materials used in the direct process reaction mixture.

The direct process for producing alkylhalosilanes is well-known and has been refined and modified in many ways since Rochow first set forth the manner in which one could obtain alkylhalosilanes by contacting alkylhalides with silicon at elevated temperatures. In a copending application filed Nov. 12, 1985, having the Ser. No. 797,372, in the name of Roland L. Halm, Oliver K. Wilding, Jr. and Regie H. Zapp, there is disclosed the use of certain phosphorous compounds in the direct process in the presence of silicon, copper and tin, to enhance the reactivity and selectivity of the reaction to produce the alkylchlorosilanes. Such phosphorous compounds are selected from elemental phosphorous, metal phosphides and phosphorous compounds capable of forming metal phosphides in the reaction mass of the direct process.

Early investigators dealt with the problems of enhancing the reactivity and selectivity of the direct process by approaching the problems from the standpoint of the physical forms of the raw materials; the treatment of the surfaces of the raw materials or the inclusion of components other than silicon and copper in the reactor feed. Thus, Nitzsche, in U.S. Pat. No. 2,666,776 issued Jan. 16, 1954, teaches that alloys of silicon and copper which also contain metals from the 5th to the 8th groups of the periodic table such as, for example, cobalt, nickel, iron or phosphorous increase the efficiency of the process if an activator, for example, a copper salt is also used.

Zoch, in U.S. Pat. No. 3,446,829, issued May 27, 1969, teaches a contact mass for the direct process containing silicon, a copper or silver catalyst and a cadmium promoter. This combination can be used as a powder mix or an alloy.

Rossmy, in German ALS 1,165,026 teaches doping of silicon by sintering powdered silicon or ferrosilicon with powdered copper alloys containing certain additives. Such additives have been described as antimony, indium, thallium, gallium, phosphorous, arsenic and bismuth. Also, in Soviet Inventions Illustrated, General Organic Section, February 1966, page 2, there is essentially described the Rossmy teaching wherein antimony and phosphorous are used in combination as an alloy, with silicon and copper.

And finally, in an article entitled "Influence of Additions of Some Elements to Silicon-Copper Alloys on Their Activity in the Reaction with Methyl Chloride," Lobusevich, N.P. et. al., translated from Zhurnal Obshchei Khimii, Vol. 34, No. 8, pp 2706–2708, August, 1964, silicon-copper alloys are described in which certain additives are used in conjunction therewith to enhance the direct process. The article shows phosphorous to be a catalytic poison at concentrations of 50 to 80 ppm based on the alloy. Further, it is noted in the summary that phosphorous when added to alloys in addition to promoters, considerably improves the catalytic property of the silicon-copper alloys. It fails, however, to suggest which promoters will or will not improve this property.

Thus, collectively, the prior art teaches that combinations of silicon-copper alloys and certain other materials can be used to affect the reactivity or selectivity of the direct process. These combinations can take the form of alloys or mixed powders, or the like, and can be used directly in the process. All of the prior art teaches alloys i.e. the melting together of certain components, but the prior art does not teach the production of silicon for the direct process wherein the level of phosphorous in the silicon is controlled such that known amounts of phosphorous are introduced to the direct process reactor. It was found quite unexpectedly that not only could silicon be treated with certain phosphorous compounds during refining, but that beneficial phosphorous compounds survived the rigors of refining and, they were the compounds that contributed to enhanced reactivity and selectivity in the direct process.

THE INVENTION

What is disclosed herein as the invention therefore is a method of improving the performance of a process for the manufacture of alkylhalosilanes, said process comprising, contacting an alkylhalide with silicon, at a temperature of 250° to 350° C., in the presence of tin or tin compounds, and copper or copper compounds, wherein there is at least also present, 25 to 2500 parts per million based on the silicon in the reaction mass, of a phosphorous promoter, which method comprises controlling the level of the phosphorous promoter in the silicon by incorporating and controlling the level of certain nonvolatile, phosphorous compounds in the mass of the silicon as it is being refined.

Also disclosed is a composition which is the silicon produced by the inventive method disclosed herein.

The key to the invention is the use of phosphorous compounds in the production of silicon which are nonvolatile and are either reducible under the conditions of silicon refining, or are already in the reduced form when they are added to the silicon which is being refined.

It is believed that the phosphorous compounds which are effective in the direct process under the influence of tin or tin compounds are the phosphides. Therefore, any phosphorous compounds which are not volatile under the conditions of silicon refining and which are in the reduced form or reducible to phosphides are the preferred compounds for use in this invention. Sometimes it is desirable that the phosphides themselves be added to the silicon during the refining thereof and sometimes it is desirable that the phosphorous compounds being added to the silicon are themselves alloyed with some other element or are in a reducible form.

Examples of phosphorous compounds useful in this invention are tricalcium phosphate and the phosphides, such as, for example, aluminum phosphide, calcium phosphide, copper phosphide and iron phosphide. Also, certain alloys are useful herein such as copper-phosphorous alloys wherein the ratio of copper to phosphorous can be varied widely.

Silicon produced by the inventive method herein is produced by the same essential means by which silicon and siliconferro alloys are being produced commercially with the exception of the use of the phosphorous compounds during refining. In the method of this invention, the key element is the control of the amount of phosphorous compound that goes into the refined silicon so that the resulting silicon will have the proper amounts of reduced phosphorous available for the direct process.

The direct process, as it is disclosed and set forth in the copending application Ser. No. 797,372 is incorporated herein by reference for what it teaches about the direct process and the catalysis thereof, specifically, it should be noted that zinc and/or zinc compounds can form part of the catalyst in the direct process when using the silicon produced by the method of the instant invention. Further, it is also beneficial when the direct process charge includes aluminum and iron therefore, there can be used with the silicon produced by the method of this invention, based on silicon, 100 to 10,000 parts per million of zinc; 0.02 to 1 weight percent aluminum and up to 1 weight percent of iron, such quantities are based on the metal actually present in the compositions.

Silicon is typically produced in a submerged electric arc furnace via carbothermic reduction of silicon dioxide ($SiO_2$) with a solid carbonaceous reducing agent. The silicon dioxide may be in the form of quartz, fused or fume silica or the like. The carbonaceous material may be in the form of coke, coal, wood chips, and other forms of carbon containing materials. The feeding of the solid reactants into the silicon furnace can be effected by conventional means such as gravity feed or gas pressure in combination with a gas-lock valve, screw feeders, pneumatic conveyors, and the like. The silicon dioxide and reducing agent may be fed alternately, first as a mixture of silicon dioxide and the reducing agent, and then as silicon dioxide by itself, or the reactants can all be fed simultaneously. It is known that certain quartz components contain higher phosphorous levels than others. Also, it is known that the electrodes in the furnace also contribute some impurities to the final silicon product. Further, the reducing agents used in the process provide another source of contaminants. The form of the silicon dioxide used in the method for producing silicon can take the form of powders, granules, lumps, pebbles, pellets and briquettes and the reducing agent takes the form of powders, granules, chips, lumps, pellets, and briquettes.

Recovery of the molten silicon for refining can be handled by any conventional means for removal of the silicon from the reaction zone of the furnace such as by batch or continuous tapping.

This invention contemplates adding the phosphorous compound to the unrefined molten silicon. Thereafter, refining can be carried out without any deleterious effect on the phosphorous compound in the silicon.

It has been determined by experimentation that oxygen refining in this invention gives less than an optimal result but that the effect of the phosphorous is still notable.

This invention also contemplates the addition of the phosphorous compounds to the molten silicon during or after refining. Thus, any means of refining the silicon is considered to be within the scope of this invention as the inventors have not found any means of refining which appears to be deleterious to the phosphorous-containing silicon.

This invention also contemplates the addition of phosphorous to the silicon when rice hulls are used as a heat insulator in silicon refining. When rice hulls are used in this manner, they are used on top of the molten silicon to retain heat. During this period of time, phosphorous leaches into the silicon from the rice hulls.

By appropriately controlling the contact of the rice hulls, one can control the amount of phosphorous in the silicon. This is one method within the scope of this invention for introducing phosphorous into silicon after refining.

The success of the silicon process is measured by the retention of phosphorous in the silicon and the effect of such silicon when used in the direct process. Enhanced activity is measured by the weight percent of $(CH_3)_2SiCl_2$ that is obtained; the ratio of $CH_3SiCl_3$ to $(CH_3)_2SiCl_2$ and the percent silicon converted to useful products, expressed in these examples as $Me_2$/weight percent, $Me/Me_2$ ratio and Si conversion (Weight %), respectively. A high $Me_2$ weight percent; low $Me/Me_2$ ratio and high Si conversion all indicate excellent activity of the treated silicon.

The direct process tests were carried out mostly on laboratory scale runs with some data obtained on large scale equipment.

The examples are provided to illustrate the detailed points of the invention and they should not be construed as limiting the invention as it is set forth in the appended claims.

The reactor used for these examples is similar to that described in Maas, et al. U.S. Pat. No 4,218,387 and is familiar to those skilled in the art for producing methylchlorosilanes using silicon and methylchloride. In general, the reaction is carried out by passing the methyl chloride, in vapor or gas form, over the surface of the silicon charge while maintaining the silicon charge at an elevated temperature. The heating of the reactant mixture is carried out, in this case, by immersing the reactor in a sand bath as a heat transfer medium.

The products of the reaction and any unreacted materials are condensed and collected in cold traps immersed in dry ice and alcohol. The products and unreacted materials are evaluated by gas chromatography by pouring the collected materials into cooled bottles (dry ice/isopropanol), cooling the chromatograph syringes and injecting samples into the gas chromatograph as quickly as possible.

The charge for the direct process reactor is prepared by grinding silicon and shaking the ground silicon in a bottle for two or three minutes with any other solid ingredients desired to be included in the reaction. The charge is placed in the reactor and the reactor is closed and weighed to give initial charge weights. The gas flow for fluidization is started. The reactor is immersed in the sand bath. The receivers for the effluent are also weighed and then connected by tubes to the reactor. The reactor is heated by the sand bath and the bath is continuously fluidized to maintain close tolerances on the temperature.

The receiver (cold traps) are placed in the dry ice baths. After a few minutes the methylchloride flow to the reactor is started. After certain periods of time and at varying temperatures which are described in detail below, the methylchloride flow is terminated, and the receivers are disconnected and weighed prior to analysis. The reactor is removed from the sand bath after cooling and it is also weighed. This procedure is used essentially as described, throughout the examples herein.

For purposes of interpreting these examples and evaluating the results, the following apply:

$$\text{Me/Me}_2 \text{ ratio} = \frac{\text{Weight \% CH}_3\text{SiCl}_3}{\text{Weight \% (CH}_3)_2\text{SiCl}_2}$$

$$\% \text{ Si Conversion} = 100 \left( 1 - \frac{\text{Amount Silicon left in charge}}{\text{Total amount of silicon charged}} \right)$$

EXAMPLE 1

Several controls were used in these experiments in order to compare against the results using the invention. Three controls were designated: control #1 - was a conventionally smelted and unrefined silicon that had essentially no phosphorous in it; control #2 - was a conventionally smelted and unrefined silicon which contained, after smelting, about 14 ppm of phosphorous and, control #3 - was a conventionally smelted and oxygen refined silicon which contained on the average about 32 ppm of phosphorous.

In this example, several samples were prepared by smelting silicon as in control #2 and injecting the phosphorous compounds into the smelted silicon during refining using a NaCl technique in which NaCl is vaporized and flowed directly into the molten silicon tapped from the smelting furnace. The NaCl used in these examples was purchased from Morton Salt Co., a division of Morton-Thiokol, Ind. and had the designation 50/50 flour salt unless the designation is indicated otherwise in the examples. "Powder usage" is reported in g/100 gms of silicon and is the amount of powder injected in grams in the refining step. Generally, in these examples, argon was the injection gas unless otherwise designated. The tricalcium phosphate (TCP) used in these examples was purchased from Mallinkrodt, Inc. and is designated as $Ca_{10}(OH)_2(PO_4)_6$ Analytical Reagent (Lot KPVA) Number 4288.

In this example, samples "$A_1$" and "$A_2$" made by injecting NaCl and TCP. It should be noted that NaCl contains about 1.75 weight % TCP as an anticaking agent. The results are shown on table I. This example illustrates that a non-volatile phosphorous compound, when added to molten silicon, results in a phosphorous-containing silicon wherein the phosphorous is in a form to enhance the reactivity and selectivity of the reactions of the direct process, when such a treated silicon is used therein.

TABLE I

Comparison of Treated and Untreated Silicon Using a Non-volatile Phosphorous Compound

| Sample | Additive Injected g/100 gms Si | Analytical on the Melted Silicon in ppm | | | | Me$_2$ Weight % | Me/Me$_2$ Ratio | Si Conv. Weight % |
|---|---|---|---|---|---|---|---|---|
| | | Al | Ca | Fe | P | | | |
| Control #1 | 0 | 4100 | 5300 | 3200 | 0 | 81.6 | 0.11 | 77.8 |
| Control #2 | 0 | 4500 | 1900 | 4900 | 14 | 84.6 | 0.08 | 80.7 |
| Control #3 | 0 | 2170 | 250 | 2130 | 32 | 83.5 | 0.09 | 50.0 |
| Control #3 | 0 | 2520 | 280 | 3620 | 33 | 84.6 | 0.08 | 59.9 |
| A$_1$ | 0.50[1] | 2520 | 330 | 3560 | 148 | 90.5 | 0.04 | 82.0 |
| A$_2$ | 0.49[2] | 2760 | 430 | 3450 | 69 | 88.0 | 0.06 | 79.4 |

[1] 12.1 Weight % TCP added to NaCl.
[2] 13.1 Weight % TCP added to NaCl.

EXAMPLE 2

Comparison of refining technologies and, refining using this invention:

Several samples of silicon were refined by varying techniques and the results were compared to silicon refined according to one aspect of this invention. These runs were carried out on a small scale induction furnace. The injection temperature for these samples ranged from 1500° C. to 1765° C. The gas flow rates ranged from 75 ml/minute to 310 ml/minute. The total volume of gas injected per sample ranged from about 0.2 scf/lb. to about 1.3 scf/lb. The results are reported on table II. Control #4 is an average of 23 runs using Cl$_2$ refining without the addition of any phosphorous. The additive injected number is thus the g Cl$_2$/100 gms of Si used. Control #5 is an average of 17 runs using O$_2$ refining without the addition of any phosphorous. The additive injected usage number is thus gO$_2$/100 gms of Si used. Sample "A" falls within the scope of this invention and is an average of 24 runs using the earlier defined NaCl and TCP injection technique for the molten silicon. The additive injected in this sample varied form 0.7 to 3.17.

TABLE II

Comparison of Refining Techniques with the Instant Invention

| Sample | Additive Injected g/100 gms Si | Me$_2$ Weight % | Me/Me$_2$ Ratio | Si Conv. Weight % |
|---|---|---|---|---|
| Control #1 | 0 | 81.6 | 0.11 | 77.8 |
| Control #2 | 0 | 84.6 | 0.08 | 80.7 |
| Control #3 | 0 | 83.5 | 0.09 | 50.0 |
| Control #3 | 0 | 84.6 | 0.08 | 59.9 |
| Control #4 | 2.25 | 86.6 | 0.07 | 66.4 |
| Control #5 | 1.96 | 86.1 | 0.07 | 45.8 |
| A | 1.75 | 88.7 | 0.06 | 74.1 |

EXAMPLE 3

Several samples were prepared and refined using NaCl and TCP injection where the type of injection gas; it's flow rate and, it's volume were varied to determine the effect on the products of the process of the instant invention. The injection temperature ranged from 1620° C. to 1640° C. The results are shown in Table III.

TABLE III

Effect of Type of Gas, Volume of Gas and Flow Rate

| Sample | Inject. Gas Used | Gas Flow Rate ml/min. | Gas Volume cu. ft./lb. Si | Additive Injected g/100 gms Si | Phosphorous in ppm | $Me_2$ Weight % | $Me/Me_2$ Ratio | Si Conv. Weight % |
|---|---|---|---|---|---|---|---|---|
| A | $N_2$ | 250 | 0.67 | 2.09 | 130 | 86 | .075 | 67.1 |
| B | $N_2$ | 290 | 0.76 | 1.89 | 110 | 88.9 | .055 | 48.6 |
| C | $N_2$ | 250 | 0.60 | 1.89 | 130 | 87.9 | .070 | 59.1 |
| D | Air | 240 | 0.72 | 2.10 | NA | 83.0 | .090 | 52.8 |
| E | Argon | 190 | 0.58 | 2.00 | 160 | 91.9 | .040 | 60.7 |
| F | Argon | 121 | 0.58 | 2.30 | 220 | 90.1 | .050 | 62.1 |
| G | $O_2$ | 211 | 0.36 | 1.18 | 33 | 89.4 | .055 | 48.9 |
| Control #3 | $O_2$ | NA | 0.14 | 0 | 33 | 83.5 | .090 | 50.0 |

EXAMPLE 4

This example compares the addition of TCP to the molten silicon, as compared to the addition of TCP and NaCl simultaneously. The injection temperature ranged from 1620° C. to about 1645° C. Sample A was injected with 0.99 grams of powdered NaCl containing 17% TCP and sample B was injected with reagent grade TCP. The results are recorded on Table IV.

TABLE IV

TCP Injection vs TCP and NaCl

| Sample | Additive Injected gm./100 grams Si | Phosphorous in ppm | $Me_2$ Weight % | $Me/Me_2$ Ratio | Si Conv. Weight % |
|---|---|---|---|---|---|
| A | 0.5 | 62 | 89.8 | 0.050 | 69.0 |
| B | 0.32 | 330 | 88.9 | 0.065 | 74.4 |
| Control #3 | 0 | 33 | 83.5 | 0.090 | 50.0 |

What is claimed is:

1. A method of improving the performance of a process for the manufacture of alkylhalosilanes, said process comprising, contacting an alkylhalide with silicon, at a temperature of 250° C. to 350° C., in the presence of tin or tin compounds, and copper or copper compounds, wherein there is at least also present, 25 to 2500 parts per million based on the silicon in the reaction mass, of a phosphorous promoter, which method comprises controlling the level of the phosphorous promoter in the silicon by incorporating a non-volatile phosphorous compound in the molten mass of the silicon after the removal of the molten mass of the silicon from the reaction zone of the furnace in which the silicon is produced.

2. A method as claimed in claim 1 wherein the phosphorous compound incorporated is in the reduced form.

3. A method as claimed in claim 2 wherein the phosphorous compound is a phosphide.

4. A method as claimed in claim 3 wherein the phosphide is calcium phosphide.

5. A method as claimed in claim 3 wherein the phosphide is copper phosphide.

6. A method as claimed in claim 3 wherein the phosphide is aluminum phosphide.

7. A method as claimed in claim 3 wherein the phosphide is iron phosphide.

8. A method as claimed in claim 1 wherein the non-volatile, phosphorous compound is added to the molten mass of the silicon prior to refining the silicon.

9. A method as claimed in claim 1 wherein the non-volatile, phosphorous compound is added to the molten mass of the silicon after the silicon is refined.

10. A method as claimed in claim 1 wherein the non-volatile, phosphorous compound is added to the molten mass of the silicon during refining.

11. A method as claimed in claim 1 further comprising refining the molten mass of silicon using NaCl injection.

12. A method as claimed in claim 1 further comprising refining the molten mass of silicon using air.

13. A method as claimed in claim 1 further comprising refining the molten mass of silicon using oxygen.

14. A method as claimed in claim 1 further comprising refining the molten mass of silicon using chlorine.

15. A method as claimed in claim 1 further comprising refining the molten mass of silicon using argon.

16. A method as claimed in claim 1 further comprising refining the molten mass of silicon using nitrogen.

17. A method as claimed in claim 8 wherein the phosphorous compound incorporated is reducible under the conditions of silicon refining.

18. A method as claimed in claim 10 wherein the phosphorous compound incorporated is reducible under the conditions of silicon refining.

* * * * *